United States Patent [19]

Adsetts

[11] 4,145,400

[45] Mar. 20, 1979

[54] PROCESS FOR THE PREPARATION OF PLURAL METAL CRYSTALLINE COMPOUNDS

[75] Inventor: John R. Adsetts, Stockton-on-Tees, England

[73] Assignee: Imperial Chemical Industries Limited, London, England

[21] Appl. No.: 787,277

[22] Filed: Apr. 12, 1977

[30] Foreign Application Priority Data

Apr. 30, 1976 [GB] United Kingdom ............... 17702/76

[51] Int. Cl.$^2$ ........................ C01F 7/00; C01G 51/06; C01G 53/06

[52] U.S. Cl. ................................. 423/419 P; 423/593; 423/600; 252/466 J; 252/470; 252/475; 260/676 R

[58] Field of Search ..................... 423/593; 252/466 J, 252/470; 423/600, 419 P

[56] References Cited

U.S. PATENT DOCUMENTS

| | | | |
|---|---|---|---|
| 3,539,306 | 11/1970 | Kumura et al. | 423/593 |
| 3,650,704 | 3/1972 | Kumura et al. | 423/415 |
| 3,865,753 | 2/1975 | Broecker et al. | 252/466 J |
| 3,879,523 | 4/1975 | Miyata et al. | 423/593 |
| 3,912,775 | 10/1975 | Broecker et al. | 252/466 J |
| 3,941,721 | 3/1976 | Broecker et al. | 252/466 J |

FOREIGN PATENT DOCUMENTS

| | | | |
|---|---|---|---|
| 49-40075 | 10/1974 | Japan | 252/466 J |
| 49-40076 | 10/1974 | Japan | 252/466 J |
| 1342020 | 12/1973 | United Kingdom | 252/466 J |

*Primary Examiner*—Herbert T. Carter
*Attorney, Agent, or Firm*—Cushman, Darby & Cushman

[57] ABSTRACT

A crystalline compound is made by reacting salts of at least one divalent metal and at least one trivalent metal in aqueous solution with sodium carbonate and ageing the resulting precipitate in alkaline conditions until a substantial increase in crystallinity has been obtained.

4 Claims, No Drawings

PROCESS FOR THE PREPARATION OF PLURAL METAL CRYSTALLINE COMPOUNDS

The invention relates to a process of making crystalline compounds by co-precipitation, converting such compounds to oxidic compositions and making catalysts from certain of the oxidic compositions.

It has recently recognised that the products formed by co-precipitating thermally decomposable compounds of divalent and trivalent metals with hydroxyl ions, divalent anions and water can in favourable conditions be crystalline and have a composition according to a defined formula. When the divalent anion is carbonate, however, attempts to form such crystalline compounds by reaction of the metal salts with the most readily available carbonate, sodium carbonate, tend to be unsuccessful unless the first-formed precipitate is aged for a long period.

We have now found a simpler, shorter, method of producing such crystalline compounds by co-precipitation with sodium carbonate.

According to the invention a method of making a crystalline compound comprises reacting salts of at least one divalent metal and at least one trivalent metal in aqueous solution with sodium carbonate and ageing the resulting precipitate in conditions at least as alkaline as 0.1 molar aqueous sodium carbonate until a substantial increase in crystallinity has been obtained.

In this specification the composition of the compounds and materials derived from them will (unless otherwise stated) by expressed as percentages by weight on the constituent non-volatile in air at 900° C. Where the Periodic Table is referred to, it is the version set forth in "Abridgments of Specifications" published by the UK Patent Office.

Preferred crystalline compounds have a composition expressed by the general formula

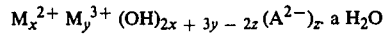

$$M_x^{2+} M_y^{3+} (OH)_{2x + 3y - 2z} (A^{2-})_z \, a\, H_2O \qquad (I)$$

in which
- $M^{2+}$ is one or more divalent metals that are normally solid;
- $M^{3+}$ is one or more trivalent metals;
- $A^{2-}$ is a divalent inorganic anion; and
- x, y, z and a are positive whole or fractional numbers that satisfy the relationships:
  - $x/y$ is between 0.25 and 8.0;
  - $z/(x + y)$ is between 0.167 and 0.05; and
  - $a/(x + y)$ is between 0.25 and 1.0.

In such compounds preferably $x = 2$ to 16, $y = 2$, $z = 0.5$ to 2.5, $a = 1.5$ to 6.0 subject to the condition that $2x + 3y - 2z$ is not less than 7.5 or greater than 34; and more preferably $x = 2$ to 8, $y = 2$, $z = 0.5$ to 1.4 and $a = 1.5$ to 5.0 subject to the condition that $2x + 3y - 2z$ is not less than 7.5 or greater than 20. Very suitably $x = 6$, $y = 2$, $z = 1$ and $a = 4$.

In the compounds the divalent metal can be one or more of those in Groups IIA, VIIA, VIII, IIB and IVB of the Periodic Table. The trivalent metal can be one or more of those in Groups IIIA (including rare earths), IVA, VA, VIA, VIIA and VIII, IIIB and VB of the Periodic Table. (It will be appreciated that some of the metals present in the compounds and/or starting materials are not in their most stable valency state, and consequently that precautions are taken when necessary to maintain a neutral, oxidising or reducing atmosphere).

The metals may be chosen so that at least a portion of the divalent metal and/or the trivalent metal present is a metal incapable of exerting more than one cationic valency. Thus, for examples, the divalent metal constituent may be or include one or more of beryllium, magnesium, calcium, strontium, barium, zinc or cadmium. Alternatively or in addition the trivalent metal constituent may be or include one or more of aluminum, scandium, yttrium and the rare earth metals. A very useful class of the compounds has as its metal constituents, both divalent and trivalent, those that are capable of forming together mixed oxides having the spinel structure. In another useful class the same metal provides both divalent and trivalent cations in the compound; iron is the most important example.

The divalent anion is conveniently carbonate but others can be present instead or in partial substitution, according to the use to which the compound is to be put.

Which metals are present in the compounds depends on the uses to which the compounds are to be put. For certain medicinal purposes the divalent metal may be magnesium and the trivalent metal aluminum. In a catalyst intermediate the divalent metal may be for example manganese, iron, cobalt, nickel, copper or zinc, alone or in combinations with each other or with magnesium or other Group IIA metals; the trivalent metal may be a Group IIIA metal or vanadium, chromium, manganese, iron, cobalt or nickel, alone or in combinations with each other. Particularly useful catalyst intermediate compounds contain (i) copper, zinc and aluminum, (ii) copper, zinc and chromium or vanadium, (iii) nickel or cobalt, with aluminum, and (iv) nickel or cobalt with magnesium and aluminum.

In forming the precipitate the metal salts are preferably nitrates, especially if it is to be converted to a catayst. The sodium carbonate is used preferably in molar excess of the metal salts giving a slurry pH up to 4 units above neutrality, and any manner or mixing with the metal salts may be used. The temperature of the precipitation reaction is preferably in the range 50°–100° C. During precipitation carbon dioxide is evolved; if desired, the slurry containing the precipitate can be heated to drive out any remaining carbon dioxide before adjusting alkalinity for the ageing step.

In ageing the precipitate, the alkaline conditions are obtained preferably by adding an alkali metal hydroxide. The quantity of alkali metal hydroxide, calculated as equivalent sodium hydroxide, added for the ageing step is suitably in the range 0.1 to 2.0 g per g of divalent metal in the crystalline compound to be produced.

After ageing, the precipitate is washed, preferably so as to leave in the solid phase a content of alkali metal compounds less than 0.5% w/w calculated as equivalent $K_2O$.

The invention includes methods of making oxidic compositions by thermal decomposition of the crystalline compounds. In order to obtain high surface area and consequently high adsorptive capacity and/or catalytic activity the temperature of thermal decomposition is preferably less than 600° C. and typically in the range 300°–550° C., the particular temperature depending on the compounds present and the intended use of the oxidic composition. For some purposes it may be advantageous to control closely the temperature at which the compound is dried and the rate at which it is heated from the drying temperature to the calcination temperature.

The invention includes especially the oxidic compositions in which one or more of the oxides has catalytic activity or is reducible to a metal having catalytic activity, especially those combinations set out hereinbefore.

The oxidic compositions may be processed for catalytic uses by known methods such as shaping into pieces (for example by dry-compression, extrusion or granulation) or coating on a particulate or shaped support or classifying to a required particle size. The resulting products may be used in fixed-bed, movable-bed or fluidised-bed operations.

The oxidic compositions may contain also one or more catalyst support materials, in addition to any that may have been introduced by co-precipitation or as nucleating material. Among the additional support materials that may be present are magnesia, magnesium silicates, alumina, aluminosilicates, titania, zirconia and thoria. An important class of oxide compositions described in our UK co-pending application 20621/75 is in the form of shaped units each comprising a mixture of (a) finite particles particles (for example in the size range of $10^2$ to $10^7$ Angstrom units) of the above described compounds containing nickel and/or cobalt and/or iron and/or thermal decomposition products of such compounds and (b) finite particles of the same size of the support material, which is preferably an aluminosilicate such as kaolin. The proportion of such additional catalyst support material is suitably 2-40% especially 8-25%. It has the useful property of absorbing small quantities of alkali metal compounds should it be impracticable to remove them sufficiently by washing.

The oxidic compositions may themselves be useful as catalysts. When they contain oxides reducible to the oxide by hydrogen at atmospheric pressure at or below 1000° C., the products or reduction are valuable as catalysts for use in reducing conditions, for example in hydrogenations and hydrocarbon/steam reactions.

The invention includes a process of methanation using the catalyst when it contains nickel and/or cobalt and/or iron. In such a process methanation may be the sole reaction, as when the starting mixture contains carbon monoxide and stoichiometric or excess hydrogen but no other reactive gas. Methanation may however be accompanied by the carbon monoxide/steam ("shift") reaction to give carbon dioxide and hydrogen if the starting gas contains steam and carbon monoxide and either no hydrogen or hydrogen in too low a proportion for methanation of all the carbon monoxide present. If the starting mixture contains carbon dioxide, methanation of carbon monoxide may be accompanied by the reverse shift reaction. If the starting mixture contains steam and a hydrocarbon of higher molecular weight than methane or a steam-reactive compound such as methanol, methanation may be accompanied by a reaction of the type

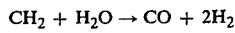

$$CH_2 + H_2O \rightarrow CO + 2H_2$$

(where "CH$_2$" is the approximate empirical formula of normally liquid hydrocarbons) or

$$CH_3OH \rightarrow CO + 2H_2$$

Thus the invention includes processes of making methane from a variety of starting materials, such as coal, liquid hydrocarbons and methanol. For steam/hydrocarbon reactions the catalyst may contain an alkali metal compound, but this is not usually necessary; preferably the alkali content, calculated as equivalent K$_2$O, is less than 0.5%, especially less than 0.1%, when the steam-hydrocarbon reaction is at under 550° C.

The temperature at the outlet of the methanation process can be as low 250° C., for example 250°-400° C., as in processes in which the exothermic heat is taken up by external cooling or by a substantial content of diluent gas, or both. Such processes may be for example the later stages in a sequence of methanations producing a natural gas substitute (at least 90% v/v of methane after steam and carbon dioxide removal), or may be carried out in the presence of recycled product gas.

The process is, however, especially useful for methanations at outlet temperature higher than 400° C., especially higher than 500, and up to for example 600°-900° C. Such methanations are important as the earlier stages in making a natural gas substitute from carbon monoxide derived from partial oxidation of coal or hydrocarbons, especially non-vaporisable hydrocarbons, or from methanol. An especially useful process has its first methanation stage at 600°-900° C. and the second at 500°-850° C. but below the temperature of the first; these are exit temperatures. Such high temperature methanation steps may be used as sources of heat for steam generation; in a proposed procedure methanatable gas is produced in an endothermic methane/steam reforming stage, piped to a site where steam is to be generated, methanated over a catalyst according to the invention, cooled in boilers and feed water heaters, and then piped back to the steam reforming stage. In such a system it is clearly of great importance to have a methanation catalyst of long-lasting activity, such as the invention provides, especially the catalyst containing the additional catalyst support material.

Such high temperature methanation using the catalyst may be carried out in the presence of moderating gases such as steam or methanation product gas, without or with carbon dioxide. The methanatable hydrogen content of the gas entering the catalyst is suitable in the range 10-15%, especially 15-30%, by volume on the total mixture, including steam.

The pressure at which methanation is carried out is typically in the range 1-100 atm, especially 5-70 atm. If gas to be methanated has been made by the reaction of normally liquid hydrocarbons with steam, methanation can be carried out using the crude product gas from such a reaction or using such a gas after removal of steam or carbon dioxide or both. Usually a small proportion of steam is present, sufficient to inhibit carbon formation. If desired, the gas can be compressed before entering the methanation stage.

Owing to the large exothermic heat of the methanation reaction, the process should be carried out in conditions allowing the temperature to be controlled and/or the heat to be recovered. Thus it may be carried out in heat exchange with boiling water under pressure or in co-current heat exchange with cool feed gas. If the starting feed is methanol, the temperature may be controlled by heat exchange with liquid water or mathanol or both. The high stability of the catalyst is, however, especially useful in processes in which the temperature is allowed to rise to the levels noted above and the gas then passed through boilers, since it makes it unnecessary to employ heat exchange or gas recycle in order to control temperature.

When the oxidic compositions contain oxides of copper, especially with zinc and possibly other components as set out hereinbefoe, they are especially useful as precursors of catalysts for methanol synthesis at temperatures in the range 160°–300° C. and pressures that are typically in the range 30–150 atm, although higher pressures can be used, or for the low temperature shift reaction at temperatures in the same range and pressures up to the condensation pressure of steam.

EXAMPLE

A solution (2 L) containing the nitrates of nickel (182 g Ni) magnesium and aluminum in the ratio 5:1:2 by metal atoms was reacted at 85° C. with a solution (4.5 L) of sodium carbonate (1215 g). At the end of precipitation the excess of sodium carbonate was 43 g per liter. The precipitate was divided into two equal parts. One part was filtered and washed, a sample (A) was taken without further treatment, and the rest of that part reslurried in 6 L of water and boiled for 4 hours, taking a sample (B) after the first 0.5 hour and a sample (C) at the end of this period. Into the other part there were dissolved 95 g of sodium hydroxide pellets. The mixture was boiled for 4 hours, taking samples (D) at 0.5 hour and (E) at the end of the period. Samples D and E were washed to remove soluble salts and sodium hydroxide. All the samples were dried at 110° C.

Constitution of the Precipitate

A sample of the precipitate was examined as powder by X-ray diffraction using Cu K alpha radiation in a diffractometer with a 1° divergence slit, a 0.2 mm receiving slit and a 1° scatter slit. The resulting diffraction pattern was indexed on the basis of a unit cell of hexagonal symmetry. The Table shows the crystal latttice Miller indices, d spacings and peak relative intensities for various Bragg angles. It is evident that by the use of sodium hydroxide it has been possible to produce by 30 minutes' boiling a material as crystalline as that produced by 4 hours' boiling without sodium hydroxide.

Preparation of Catalyst

Run D was repeated on a larger scale. The precipitate was washed very thoroughly, calcined at 380° C. for 4 hours and then ground to pass a 150 BSS sieve, such that its median particle size was about $5 \times 10^5$ Angstrom units. The powder was mixed with 20% of its weight of kaolin (passing BBS 350 sieve, median particle size $4.4 \times 10^5$ Angstrom units). The mixture was mixed with 2.5% w/w of graphite and dry-compressed into $3.6 \times 5.4$ mm squat cylindrical pellets.

Use of Catalyst in Methanation

The pellets were tested by passing over them a gas of volume percentage composition CO 31.1, $CO_2$ 24.7, $H_2$ 42.9, $N_2$ + Ar 1.2, $CH_4$ 0.1 mixed with 67.3% of its volume of steam at a dry gas volume hourly space velocity of 10000 $hour^{-1}$ and a pressure of 30 atm. abs. The inlet temperature was 398° C. and the outlet temperature 729° C. (These conditions simulate the first methanation stage in producing substitute natural gas from coal). The catalyst operated at an extremely low rate of deactivation: after 2200 hours the region of maximum temperature had advanced less than 1 inch through the catalyst bed. A further sample of this catalyst was tested at 590° C. outlet temperature using the product gas of the methanation at 729° C. after cooling that gas to 325° C. A third sample was tested at 428° C. outlet temperature using the product of the methanation at 590° C. after cooling that gas to 300° C. In each of these tests the region of maximum temperature advanced less than 1 inch in 1500 hours when operation was voluntarily stopped.

The catalyst is thus suitable for the adiabatic high temperature methanation stages of a process for producing substitute natural gas.

TABLE

| Sample | Line 003 (° 2θ) | d-Spacing (A) | | | | Peak Intensity | | | | Line Breadth (° 2θ) at ½ Peak Height | | | |
|---|---|---|---|---|---|---|---|---|---|---|---|---|---|
| | | 003 | 006 | 110 | 113 | 003 | 006 | 110+ | 113+ | 003 | 006 | 110** | 113** |
| A | 11.4 | 7.60 | 3.825 | 1.523 | 1.492 | 26 | 8.3 | 5.0 | 4.5 | 1.31 | 1.52 | 0.87 | 1.15 |
| B | 11.575 | 7.64 | 3.838 | 1.522 | 1.493 | 47 | 16.9 | 6.8 | 6.8 | 0.77 | 0.85 | 0.67 | 0.77 |
| C | 11.475 | 7.71 | 3.853 | 1.522 | 1.494 | 59 | 26.6 | 8.0 | 7.3 | 0.63 | 0.63 | 0.62 | 0.74 |
| D | 11.495 | 7.70 | 3.851 | 1.522 | 1.494 | 49 | 17.9 | 7.5 | 7.2 | 0.79 | 0.81 | 0.62 | 0.85 |
| E | 11.48 | 7.71 | 3.853 | 1.522 | 1.493 | 80 | 34.3 | 8.0 | 9.3 | 0.52 | 0.52 | 0.58 | 0.56 |

| Sample | Line 003 (° 2θ) | Equivalent Mean Cryst. size (A) | | | | Integrated Intensity* | | | |
|---|---|---|---|---|---|---|---|---|---|
| | | 003 | 006 | 110** | 113** | 003 | 006 | 110** | 113** |
| A | 11.64 | 67 | 56 | 120 | 90 | 34.0 | 12.6 | 4.4 | 5.2 |
| B | 11.575 | 119 | 106 | 170 | 140 | 36.2 | 14.4 | 4.6 | 5.3 |
| C | 11.475 | 150 | 150 | 190 | 150 | 37.0 | 16.8 | 4.9 | 5.4 |
| D | 11.495 | 115 | 112 | 190 | 125 | 38.8 | 14.6 | 4.7 | 6.1 |
| E | 11.48 | 198 | 198 | 210 | 220 | 41.6 | 17.8 | 4.6 | 5.2 |

*i.e. product of peak intensity and line breadth at half peak height
**Figures in these columns are approximate owing to incomplete resolution of the 110 and 113 peaks.

I claim:

1. A method of making a crystalline compound having a composition expressed by the general formula:

$$M_x^{2+} Al_2 (OH)_{16} CO_3 \cdot 4H_2O$$

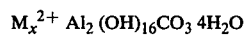

where
   $M^{2+}$ is selected from the group consisting of nickel, cobalt, and mixtures thereof; and
   x = 6
which comprises co-precipitating salts of the metal $M^{2+}$ and aluminum in aqueous solution with sodium carbonate, adding to the resulting precipitate an alkali metal hydroxide in a quantity of 0.1 to 2.0 g calculated as equivalent sodium hydroxide per gram of metal $M^{2+}$ in the precipitate, and ageing the precipitate by heating for a period to obtain a degree of crystallinity which is substantially increased when compared with the crystallinity of a precipitate aged for a similar period without the addition of alkali metal hydroxide.

2. A method according to claim 1 in which, after the ageing step, the precipitate is washed until its content of alkali metal compounds calculated as equivalent $K_2O$ on the metal oxides present, is less than 0.5% W/W.

3. A method according to claim 1 in which magnesium is present in partial substitution for nickel or cobalt.

4. A method according to claim 1 in which the increase in crystallinity corresponds to the following changes in X-ray diffraction parameters:

Line 003 Bragg angle: from 11.575° to at most 11.495°;

d spacings:
    003 — from 7.64 at least 7.70 Angstrom units;
    006 — from 3.838 to at least 3.851 Angstrom units;
peak intensities: 006 — from 16.9 to at least 17.9;
integrated intensity:
    003 — from 36.2 to at least 38.8;
    006 — from 14.4 to at least 14.6.

* * * * *